(12) United States Patent
Yozu et al.

(10) Patent No.: US 6,679,861 B2
(45) Date of Patent: Jan. 20, 2004

(54) OCCLUSION CATHETER FOR THE ASCENDING AORTA

(75) Inventors: Ryohei Yozu, Yokohama (JP);
Nobumasa Tsutsui, Nagoya (JP);
Takashi Kumeno, Aichi-ken (JP)

(73) Assignee: K.K. Vayu, Nagoya (JP)

( * ) Notice: Subject to any disclaimer, the term of this patent is extended or adjusted under 35 U.S.C. 154(b) by 19 days.

(21) Appl. No.: 09/846,002

(22) Filed: Apr. 30, 2001

(65) Prior Publication Data

US 2003/0167038 A1 Sep. 4, 2003

(30) Foreign Application Priority Data

May 29, 2000 (JP) .......................................... 2000-158152

(51) Int. Cl.[7] .............................................. A61M 29/00
(52) U.S. Cl. ............................... 604/102.01; 604/102.02
(58) Field of Search ............................ 604/6.16, 96.01, 604/102.01, 102.02, 102.03, 104, 264, 523; 606/191, 194

(56) References Cited

U.S. PATENT DOCUMENTS

| | | | | |
|---|---|---|---|---|
| 4,592,340 A | * | 6/1986 | Boyles ......................... | 600/18 |
| 4,892,519 A | * | 1/1990 | Songer et al. ......... | 604/102.03 |
| 5,024,234 A | * | 6/1991 | Leary et al. ................ | 600/467 |
| 5,046,503 A | * | 9/1991 | Schneiderman ............. | 600/446 |
| 5,312,344 A | * | 5/1994 | Grinfeld et al. ............ | 600/433 |
| 5,814,016 A | * | 9/1998 | Valley et al. ............. | 604/96.01 |
| 5,855,563 A | * | 1/1999 | Kaplan et al. ............... | 600/439 |
| 5,997,558 A | * | 12/1999 | Nash .......................... | 606/159 |
| 6,045,531 A | | 4/2000 | Davis ......................... | 604/101 |
| 6,117,105 A | * | 9/2000 | Bresnaham et al. ........ | 604/500 |
| 6,322,577 B1 | * | 11/2001 | McInnes ................... | 604/96.01 |
| 6,347,247 B1 | * | 2/2002 | Dev et al. ...................... | 607/2 |

FOREIGN PATENT DOCUMENTS

| | | | | |
|---|---|---|---|---|
| WO | 98/48884 | 11/1998 | .......... | A61M/25/10 |
| WO | 99/30766 | 6/1999 | .......... | A61M/29/00 |

* cited by examiner

Primary Examiner—Edward K. Look
Assistant Examiner—John K Fristoe, Jr.
(74) Attorney, Agent, or Firm—Davis & Bujold, PLLC

(57) ABSTRACT

An occlusion catheter for the ascending aorta capable of obstructing the blood flow within the ascending aorta without inserting through the femoral artery. The occlusion catheter is provided with a drug release aperture formed in the region, which is closer to the proximal end of the catheter tube than a balloon on the outer circumference of the distal end and which is to be located in the vicinity of the coronary ostium when the balloon is placed within the ascending aorta. The present occlusion catheter, when inserted directly into the ascending aorta in the vicinity of the heart to obstruct the blood flow therewithin, enables delivery of a cardiac muscle protective drug to the vicinity of the coronary ostium without inserting the occlusion catheter through the femoral artery in the conventional manner.

8 Claims, 15 Drawing Sheets

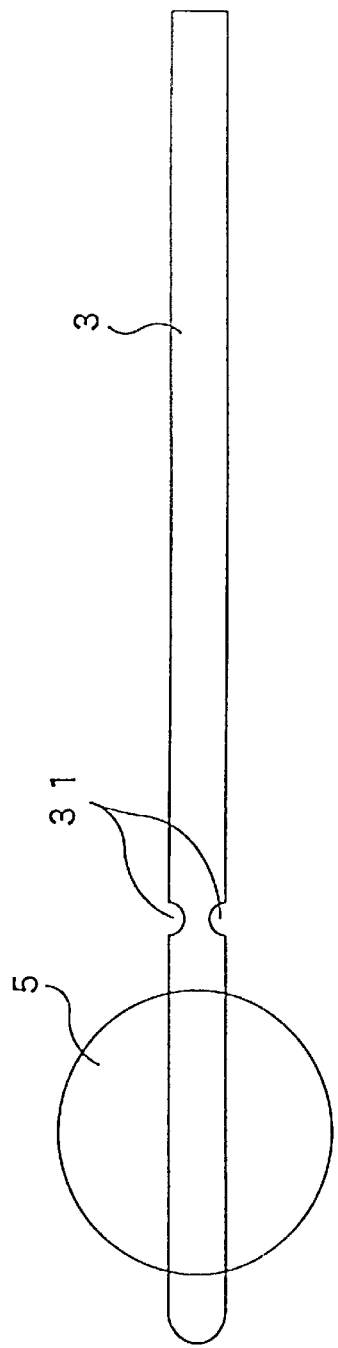
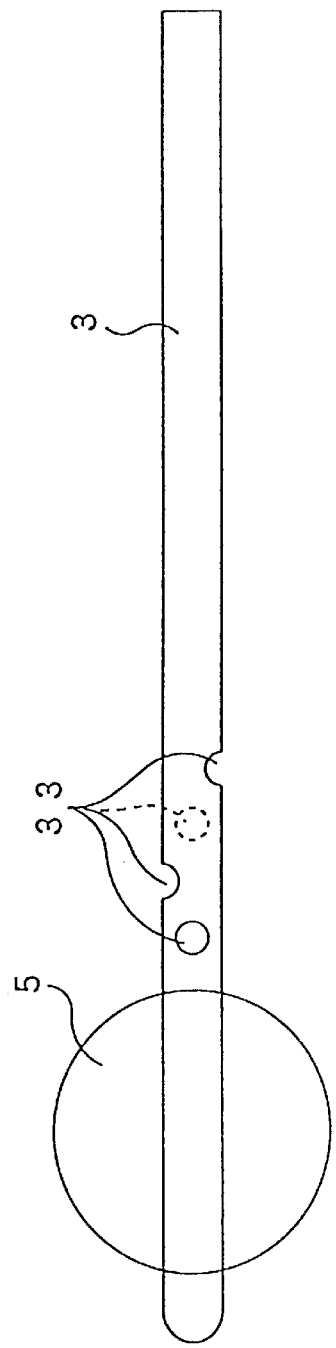
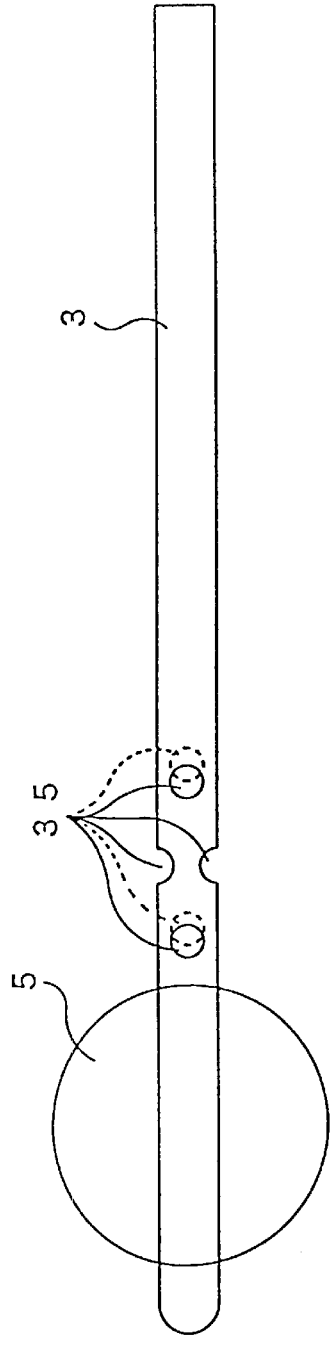

FIG. 4A
FIG. 4B
FIG. 4C
FIG. 4D
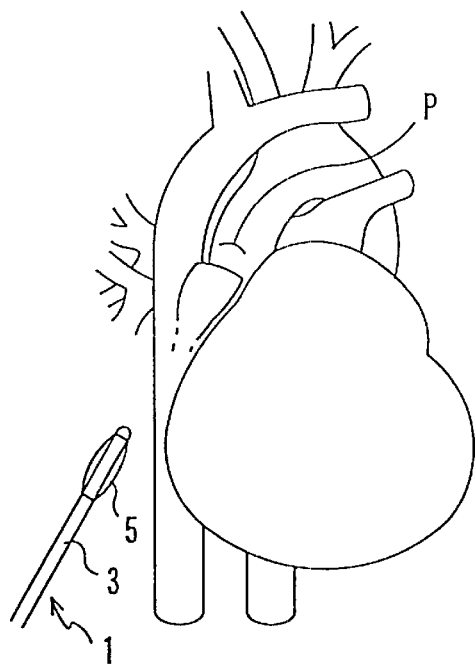
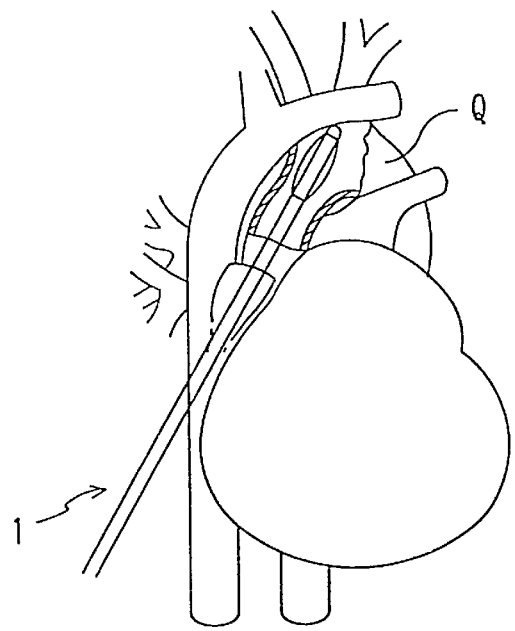
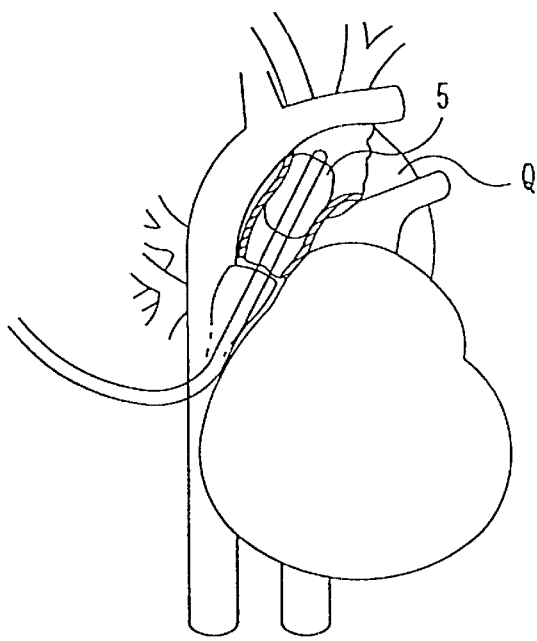
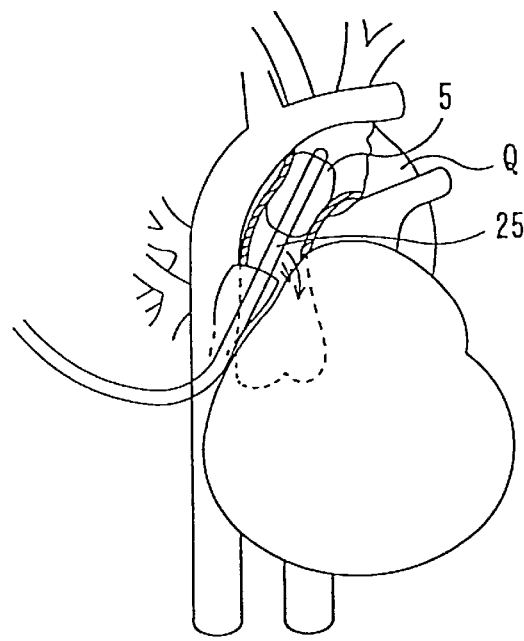

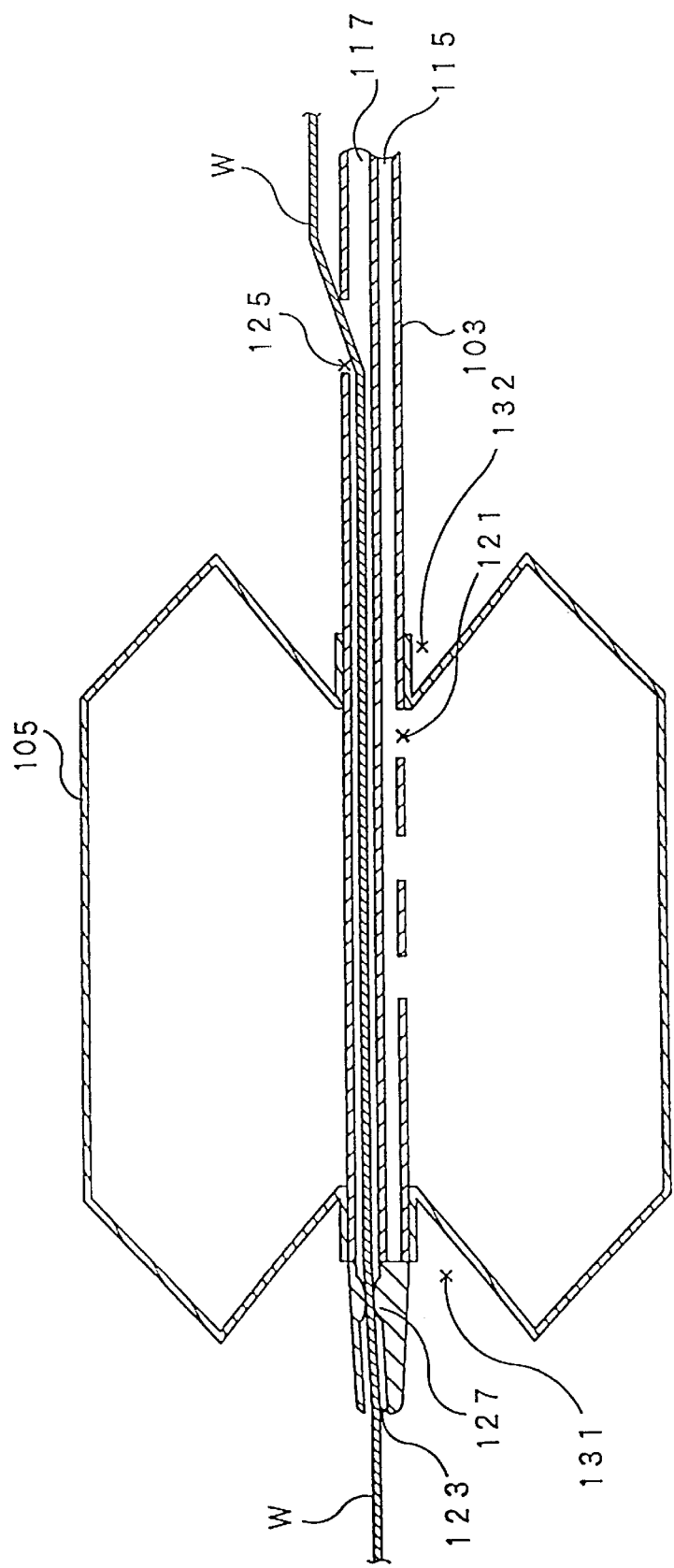

OCCLUSION CATHETER FOR THE ASCENDING AORTA

BACKGROUND OF THE INVENTION i) Field of the Invention

The present invention relates to an occlusion catheter for the ascending aorta used for obstructing the blood flow in the ascending aorta.

ii) Prior Art

When a cardiac surgery is performed, the blood flow in the ascending aorta is obstructed generally using a conventional cross-clamp through an opening in a patient's chest formed by thoracotomy.

Recently, there have been attempts to obstruct the blood flow in the ascending aorta using an occlusion catheter for the ascending aorta (hereinafter referred to as "an occlusion catheter") inserted through a femoral artery, for example, without performing an open chest operation.

An occlusion catheter of this type comprises a tube and a balloon disposed on the circumference of the distal end of the tube. The tube is inserted through the femoral artery and advanced through the thoracic aorta to the ascending aorta, in which the distal end of the tube is placed and the balloon is inflated, with the result that the blood flow is obstructed.

In another occlusion catheter, a cardiac muscle protective drug supplied from the proximal end of the tube is delivered to the distal end of the tube and released from a drug release aperture provided at the distal end of the tube.

These conventional occlusion catheters, however, have the following problems: The conventional occlusion catheter to be inserted through the femoral artery may hinder the blood flow directed to the lower limb, particularly, of a patient whose blood vessel in the lower limb is thin. In such a case an occlusion catheter of this type cannot be used.

The conventional occlusion catheter requires a guide wire in order to push the occlusion catheter throughout a long path from the femoral artery to the ascending aorta. As a result, a lumen to pass the guide wire therethrough must be provided in the tube, which leads to a relatively large diameter of the catheter and therefore a further factor of hindrance to the blood flow.

Furthermore, since the conventional occlusion catheter is long enough to extend from the femoral artery to the ascending aorta, the flow path resistance of the lumen in the tube is so large that the flow rate of the cardiac muscle protective drug cannot be easily increased. Although the flow rate of the cardiac muscle protective drug can be increased by simply having a lumen of a larger inner diameter, such a lumen necessarily requires a catheter of a larger diameter, which may hinder the blood flow toward the lower limb.

When inserted through the femoral artery, the conventional occlusion catheter may have its balloon damaged in the case where the blood vessel in the lower limb or the aorta is calcified, or cannot be easily advanced through a meandering blood vessel.

While the tube preferably is flexible enough to curve to a certain extent for better operation in the blood vessel, the tube having an excessive flexibility cannot support the balloon which is pushed by the blood flow from a pump oxygenator or the infusion pressure of the cardiac muscle protective drug. In this case, the balloon together with the tube is to be displaced from the proper indwelling position. To avoid such displacement of the balloon, a substantially hard tube is generally employed and operationality in the blood vessel is necessarily sacrificed.

The conventional occlusion catheter has a structure wherein displacement of the catheter tube in the axial direction is easily conducted to the balloon. Specifically, when the proximal end of the catheter tube is displaced in the axial direction, the distal end of the catheter tube is also displaced in the axial direction, with the result that the balloon is displaced as well. Thus, it is not easy to retain the balloon in the proper indwelling position.

SUMMARY OF THE INVENTION

Wherefore, it is an object of the present invention to provide an occlusion catheter capable of obstructing the blood flow in the ascending aorta without inserting the same through the femoral artery.

Another object of the present invention is to provide an occlusion catheter capable of maintaining the condition where the balloon is placed in the proper indwelling position.

To solve the above-mentioned problems associated with the prior art occlusion catheters, the inventors of the present invention first considered inserting an occlusion catheter directly into the ascending aorta in the vicinity of the heart after opening the chest in order to obstruct the blood flow when a cardiac surgery is performed.

This reduces the possibility of preventing the blood flow toward the lower limbs, and facilitates an increase of the flow rate of the cardiac muscle protective drug. Also, calcification or meandering of the blood vessel in the lower limb or the aorta does not present problems.

However, the above prior art occlusion catheter cannot be used to insert directly into the ascending aorta in the vicinity of the heart to obstruct the blood flow. Particularly, since the direction of inserting the occlusion catheter is opposite to the direction when the occlusion catheter is inserted through the femoral aorta, a new problem is caused that the cardiac muscle protective drug, which is released from the distal end, flows toward the lower limbs instead of being delivered to the coronary artery.

The inventors therefore completed the occlusion catheter of the present invention to also solve the new problem.

The occlusion catheter of the present invention comprises: a catheter tube having at least a first lumen and a second lumen independent of each other; and a balloon provided on the outer circumference of the distal end of the catheter tube for being inflated/deflated in accordance with supply or drainage of the fluid through the first lumen in order to obstruct the blood flow within the ascending aorta when inflated, the catheter tube being provided with a drug release aperture for releasing a drug supplied through the second lumen in the position closer to the proximal end than the site where the blood flow is obstructed by the balloon on the outer circumference of the distal end of the catheter tube.

The present occlusion catheter, even when it is inserted directly into the ascending aorta in the vicinity of the heart to obstruct the blood flow, enables delivery of a drug such as a cardiac muscle protective drug to the vicinity of the coronary ostium by supplying the drug through the second lumen.

Further, since the occlusion catheter is inserted directly into the ascending aorta in the vicinity of the heart instead of being inserted through the femoral artery in the conventional manner, the blood flow toward the lower limbs is not prevented, and the flow rate of the drug such as the cardiac muscle protective drug can easily be increased. Also, calcification or meandering of the blood vessel in the lower limb or the aorta does not present problems at the insertion of the catheter.

In another aspect of the present invention, the occlusion catheter comprises: a catheter tube having at least a first lumen and a second lumen independent of each other; and a balloon provided on the outer circumference of the distal end of the catheter tube for being inflated/deflated in accordance with supply or drainage of the fluid through the first lumen to obstruct the blood flow within the ascending aorta when inflated, the balloon having a configuration with a concavity on the outer surface at least when inflated and being joined to the catheter tube in the concavity, the catheter tube being provided with a side aperture for communicating the outside of the catheter tube and the second lumen in the different position from a concavity of the balloon, and the side aperture enabling release of a drug therefrom by supplying the drug through the second lumen.

The concavity is a region in which the balloon sinks toward its inside and also is joined to the catheter tube. The concavity may be previously formed at the time of forming the balloon or may be formed as the result of the balloon, which is made of a substantially elastic material, expanding in the axial direction of the catheter tube when inflated. With such a concavity, in the case where the catheter tube is slightly displaced in the axial direction, the concavity is deformed to expand toward the outside of the balloon in accordance with the displacement of the catheter tube and without having the balloon displaced. Thus, the balloon can easily be retained in the proper indwelling position without being displaced.

In a further aspect of the present invention, the occlusion catheter comprises: a catheter tube having at least a first lumen and a second lumen independent of each other; and a balloon provided on the outer circumference of the distal end of the catheter tube for being inflated/deflated in accordance with supply or drainage of the fluid through the first lumen to obstruct the blood flow within the ascending aorta when inflated, the balloon having a configuration with a depression in a part of the center of the balloon at least when inflated and being joined to said catheter tube in the depression, and the catheter tube being provided with a side aperture in the side wall in the depression of the balloon, for communicating the outside of the catheter tube and the second lumen to enable release of a drug from the side aperture by supplying the drug through the second lumen.

With the structure as above, when the occlusion catheter is inserted approximately perpendicular to a blood vessel, the balloon is supported by the blood vessel wall symmetrically relative to the catheter tube, and is retained in the proper indwelling position within the blood vessel. Thus, the balloon is not displaced by the blood flow from a pump oxygenator or the injection pressure of the cardiac muscle protective drug, and therefore the tube is not required to have an excessive rigidity. Also, this structure allows the balloon to be relatively small while keeping the same advantage as described above.

The above described occlusion catheter preferably has a portion, from the distal end of the catheter tube to the position a predetermined distance away from the distal end, which is reinforced by a reinforcement member. This improves the position retainability of the occlusion catheter.

In another aspect of the present invention, an occlusion catheter for the ascending aorta comprises: a catheter tube having two or more lumens, including at least a first lumen and a second lumen formed therewithin; a balloon provided on the outer circumference of the distal end of the catheter tube for being inflated/deflated in accordance with supply or drainage of the fluid through the first lumen in order to obstruct the blood flow within the ascending aorta when inflated, the catheter tube being provided with a side aperture in the position closer to the proximal end than the balloon, for communicating the outside of the catheter tube and the second lumen to enable release of a drug from the side aperture by supplying the drug through the second lumen; and a valve provided within the second lumen having a structure capable of passing a guide wire therethrough and shutting the fluid flow at least when the guide wire is not passed.

In the occlusion catheter having such a structure, the valve provided inside the second lumen allows the guide wire to pass through the valve, and the second lumen may be used as a guide wire insertion lumen.

Moreover, the valve prevents the blood in the blood vessel from flowing into the second lumen through an opening provided at the distal tip end (hereinafter referred to as "a distal end opening") of the catheter tube, while, at the same time, preventing the fluid in the second lumen from flowing out into the blood vessel. Therefore, the second lumen may be used for purposes other than guide wire insertion.

In the occlusion catheter as above, the guide wire is passed through a short section from the distal end opening to the side aperture of the catheter tube. Accordingly, when the guide wire is placed in a patient's body and a portion of the guide wire exposed to the outside of the body is relatively short, the portion can be passed through the section from the distal end opening to the side aperture of the catheter tube. Therefore, compared with a catheter having a guide wire insertion lumen throughout the length of the catheter, there is no need of using an excessively long guide wire or connecting another guide wire for extension to the guide wire.

BRIEF DESCRIPTION OF THE DRAWINGS

Preferred embodiments of the present invention will be described hereinafter with reference to the drawings, in which:

FIGS. 3A through 3C are schematic views showing modifications of the positions for forming drug release apertures;

FIGS. 4A through 4D are exemplary views illustrating how to use the occlusion catheter;

FIG. 7A is a longitudinal sectional view in the vicinity of the balloon of the occlusion catheter shown in FIG. 6;

FIG. 7B is a sectional view of the tip end of a catheter tube;

DETAILED DESCRIPTION OF THE PREFERRED EMBODIMENTS

First Embodiment

Figure 1:
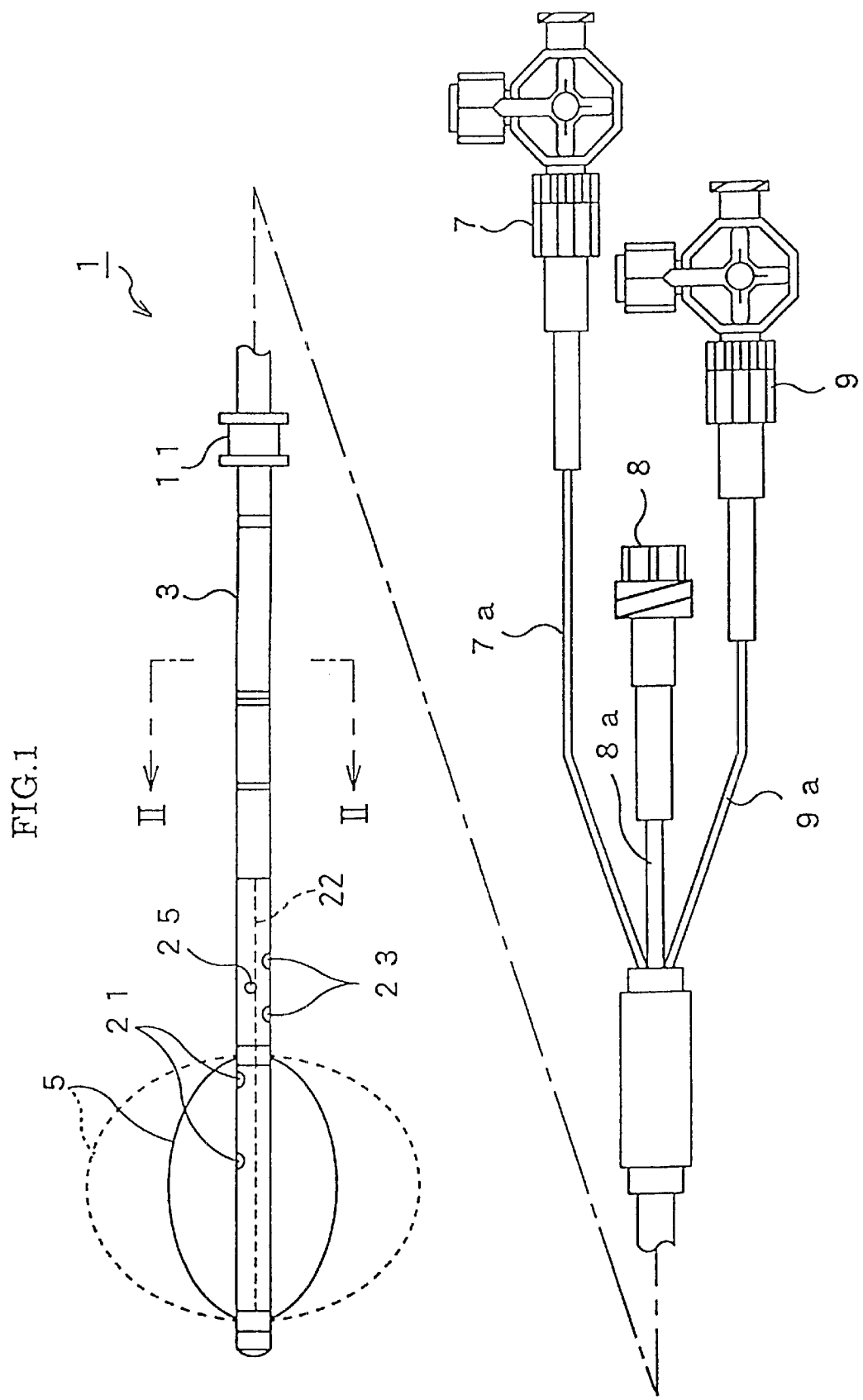
FIG. 1 is a side view of an occlusion catheter according to a first embodiment of the invention.

As shown in FIG. 1, an occlusion catheter for the ascending aorta 1 according to the present invention is provided with a catheter tube 3, a balloon 5, a first connector 7, a second connector 8, a third connector 9 and a tie cushion 11, etc.

Figure 2:
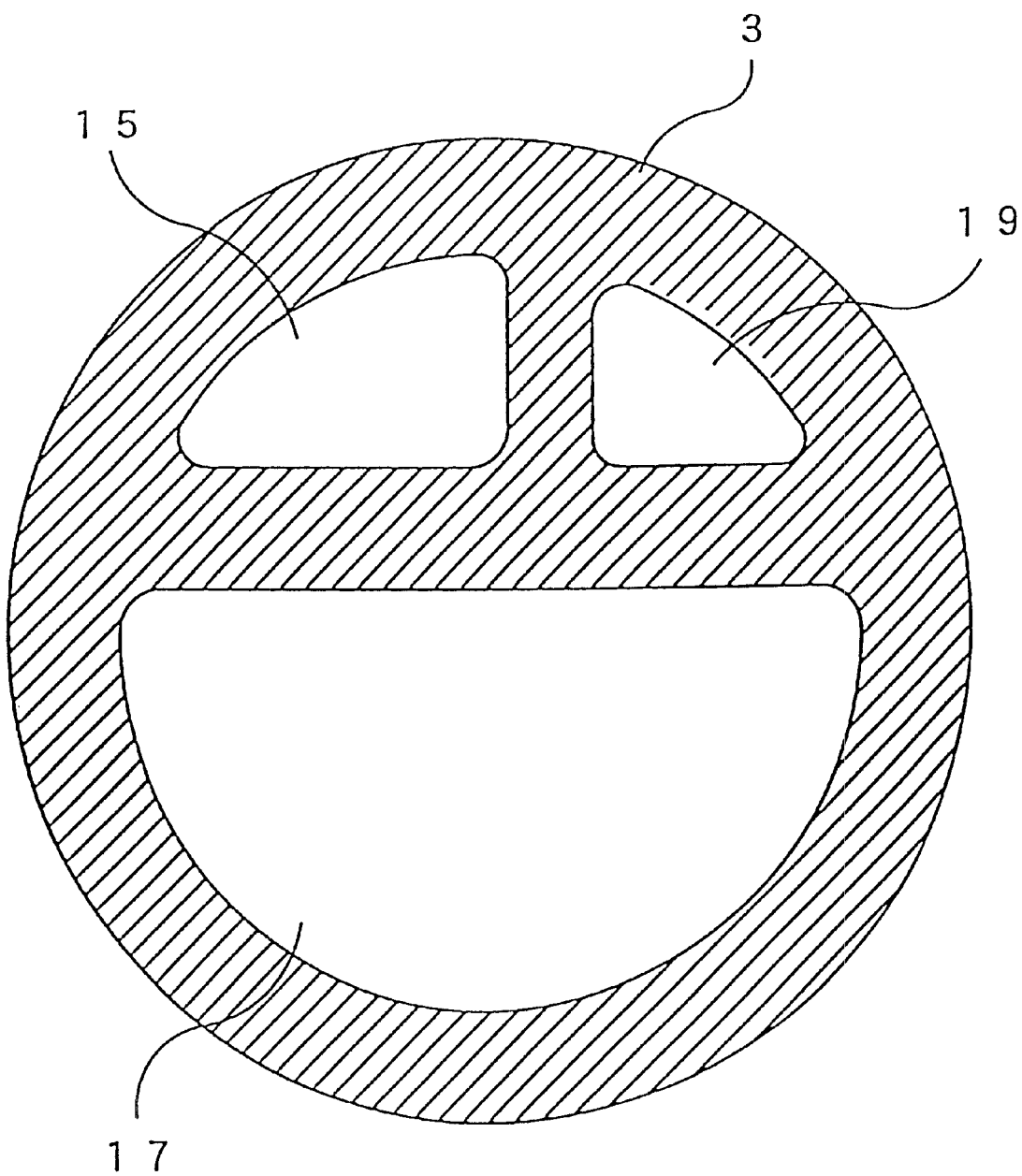
FIG. 2 is a cross-sectional view of the occlusion catheter shown in FIG. 1 taken along line II—II.

The catheter tube 3 made of polyurethane is long enough to include a portion with a length of 400 mm and an outer diameter of 3.6 mm which is insertable into a blood vessel. As shown in FIG. 2, a first lumen 15, a second lumen 17 and a third lumen 19 are formed separately from one another within the catheter tube 3.

The first lumen 15 has one end communicating with the first connector 7 through a first auxiliary tube 7a and the other end communicating with a plurality of inflation agent supply and drainage apertures 21 having a diameter of 1 mm and formed inside the balloon 5. The first lumen 15 is used as a path for guiding an inflation agent (e.g. a physiological salt solution) supplied from the first connector 7 side to the inside of the balloon 5. At least one inflation agent supply and drainage aperture 21 is preferably arranged in a region adjoining a joint of the balloon 5 and the catheter tube 3. It is because when an operation of filling the balloon 5 with the inflation agent to remove air bubbles before insertion of the catheter is performed, air bubbles can easily be removed through the above supply and drainage aperture 21 arranged in the region adjoining the above joint. It is also preferable that the circumference of the supply and drainage aperture 21 is colored (black, for example) to improve visibility and facilitate guidance of air bubbles to the supply and drainage aperture 21.

The second lumen 17 has one end communicating with the second connector 8 through a second auxiliary tube 8a and the other end communicating with drug release apertures 23 each aperture having a diameter of 1.5 mm and being formed in the side wall of the catheter tube 3 closer to the proximal end than the balloon 5. The second lumen 17 is used as a passage for guiding a drug (e.g. a cardiac muscle protective drug) injected from the second connector 8 side to the drug release aperture 23.

The third lumen 19 has one end communicating with the third connector 9 through a third auxiliary tube 9a and the other end communicating with a blood pressure measuring aperture 25 having a diameter of 0.8 mm and formed in the side wall of the catheter tube 3 closer to the proximal end than the balloon 5. The third lumen 19 is used for measuring the blood pressure outside the blood pressure measuring aperture 25 with a pressure sensor (not shown) connected to the third connector 9 via a liquid (blood, a physiological salt solution, or the like) which is introduced into the third lumen 19.

The balloon 5 is made of polyurethane and has a length of 30 mm, an outer diameter of 20 mm (the molded dimension) and a film thickness of 75 $\mu$m. The outer diameter can be increased further to such an extent that the balloon 5 occludes the ascending aorta, as indicated by a dotted line in FIG. 1.

The tie cushion 11 is a hollow cylindrical member which facilitates secure fixation of a Nelaton's tube (not shown) to the catheter tube 3 when tying them with a thread and prevents crash of the tube 3 by the external force at the same time.

It is preferable to house a metal wire 22 in the catheter tube 3 in order to improve stability when the tube 3 is placed in an indwelling position. Detailed description of the metal wire will be presented in connection with a second embodiment of the present invention.

While the two drug release apertures 23 are formed in the same direction in the above catheter tube 3, it is possible to form two drug release apertures 31 in two different directions as shown in FIG. 3A. In this case, even if one of the drug release apertures 31 is shut tight by a blood vessel wall, the drug can be surely released from the other drug release aperture 31.

To avoid the possibility of decreasing the strength of the catheter tube 3 around the region where the drug release apertures 31 are formed in the same axial position of the catheter tube 3, a plurality of drug release apertures 33 are preferably formed in different axial positions of the catheter tube 3, as shown in FIG. 3B. In the case where four drug release apertures 33 are arranged spirally as shown in FIG. 3B, these apertures are not in the same axial position of the catheter tube 3 and the drug are released in four different directions.

Releasing the drug in four different directions does not always require the drug release apertures to be arranged spirally and allows drug release apertures 35, for example, to be arranged as shown in FIG. 3C.

An example of how to use the occlusion catheter 1 will now be described.

Firstly, the chest of a patient is incised to expose the ascending aorta and the ascending aorta is perforated at an insertion site P thereon (FIG. 4A). The usual perforation at the insertion site P includes puncture using a needle to provide a hole and expansion of the hole with a dilator, but other methods may be employed.

Figure 5:
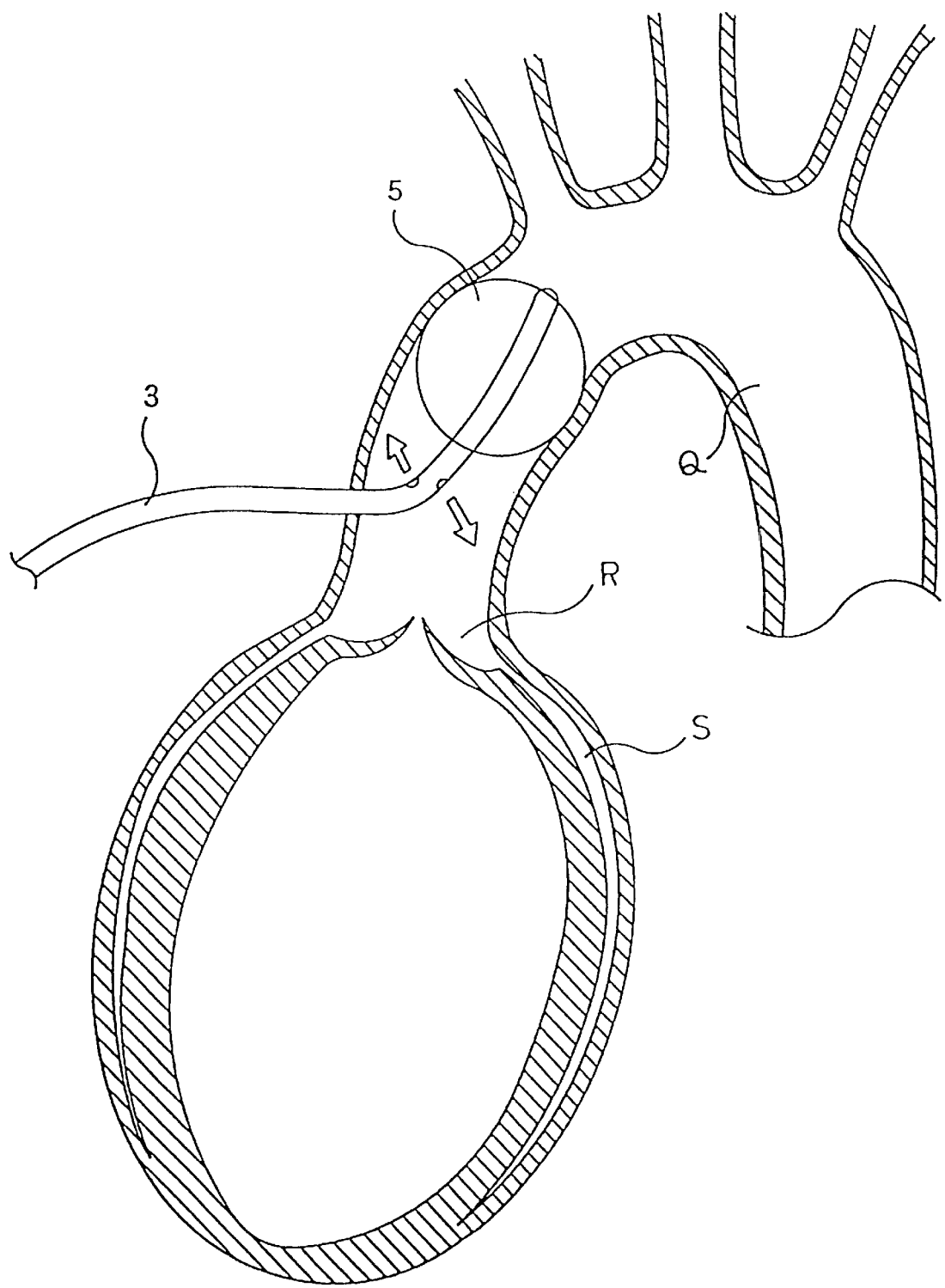
FIG. 5 is a schematic diagram showing the operational state of the above occlusion catheter.

Subsequently, the above occlusion catheter 1 is inserted into the ascending aorta Q (FIG. 4B) and then fixed by ligating the surrounding of the insertion site with a suture thread by cigarette suture technique. The suture thread used for ligation is passed through, for example, the Nelaton's tube and fixed to the Nelaton's tube in a position distant from the insertion site using a mosquito clamp or the like in order to prevent the thread from loosening in the ligated part. The Nelaton's tube in turn is fixed to the catheter tube 3 by tying the same with a thread within the region of the tie cushion 11. The balloon 5 is placed in the proper indwelling position while checking the position by X-ray fluoroscopy, and then is inflated (FIG. 4C). As a result, the ascending aorta is occluded by the balloon 5, as shown in FIG. 5. The obstruction of the blood flow is confirmed by angiography, and if necessary, a cardiac muscle protective drug is released from the drug release aperture 25 (FIG. 4D) to be delivered to the vicinity of the coronary ostium R and therefore to the coronary artery S.

As described above, use of the occlusion catheter 1 permits a surgeon when performing a cardiac surgery to insert the occlusion catheter 1 directly into the ascending aorta in the vicinity of the heart after making an incision in the chest so that the blood flow can be obstructed as well as the cardiac muscle protective drug (indicated by the arrows in FIG. 5) can be delivered to the vicinity of the coronary ostium R by supplying the cardiac muscle protective drug through the second lumen 17.

Thus, even when a cross-clamp is not or cannot be used, it is unnecessary to insert an occlusion catheter through a femoral artery, with the result that hindrance of the blood flow toward the lower limb is prevented, that the flow rate of the drug such as a cardiac muscle protective drug can be easily increased, and that a calcified or meandering blood vessel of the lower limb does not become an obstacle upon insertion of the catheter.

Second Embodiment

Figure 6:
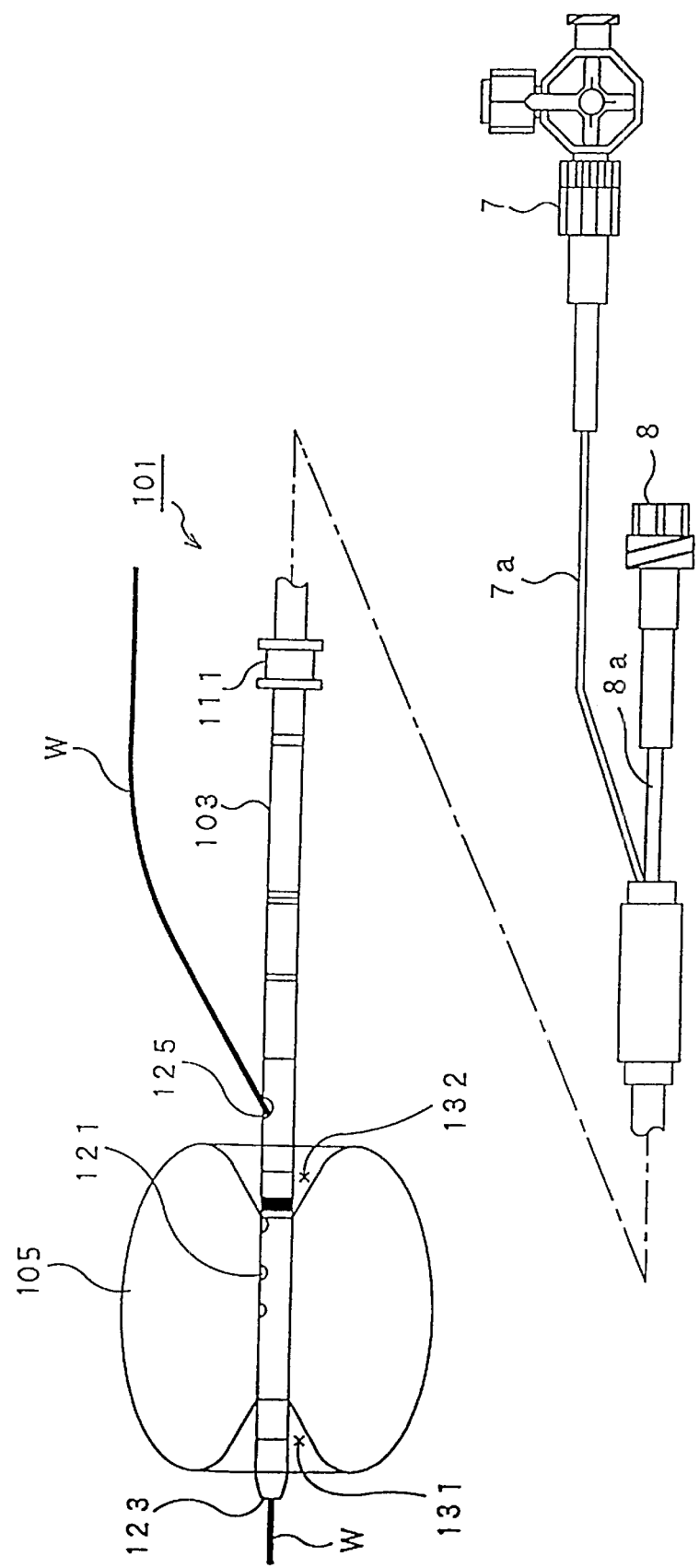
FIG. 6 is a side view of an occlusion catheter according to a second embodiment of the invention.

As shown in FIG. 6, an occlusion catheter 101 according to a second embodiment of the present invention is provided with a catheter tube 103, a balloon 105, a first connector 7, a second connector 8, a third connector 9 and a tie cushion 111, etc.

The catheter tube 103 made of polyurethane is long, and a first lumen 115 and a second lumen 117 are formed therein separately from each other as shown in FIG. 7A.

The first lumen 115 has one end communicating with the first connector 7 through a first auxiliary tube 7a (see FIG. 6) and the other end communicating with a plurality of inflation agent supply and drainage apertures 121 formed inside the balloon 105. The first lumen 115 is used as a passage for guiding an inflation agent (e.g. a physiological salt solution) supplied from the first connector 7 side to the inside of the balloon 105.

The second lumen 117 has one end communicating with the second connector 8 through a second auxiliary tube 8a, the other end communicating with a distal end opening 123 formed at the distal end of the catheter tube 103, and a side aperture 125 communicating the second lumen 117 and the outside of the catheter tube 103, the side aperture 125 being arranged closer to the proximal end than the balloon 105. One portion of the second lumen 117 from the distal end opening 123 to the side aperture 125 is used for passing a guide wire W therethrough. The other portion of the second lumen 117 from the side aperture 125 to the second connector 8 is used for guiding a drug (e.g. a cardiac muscle protective drug) injected from the second connector 8 side to the side aperture 125, and for measuring the blood pressure outside the side aperture 125 with a pressure sensor (not shown) connected to the second connector 8.

The second lumen 117 is provided with a valve 127 therein, which is made of an elastic body having rubber elasticity (e.g. silicone rubber in the present embodiment). The valve 127 has an insertion hole to pass the guide wire W therethrough, the insertion hole being shut tight to prevent the fluid from flowing through at least when the guide wire is not inserted into the insertion hole, as shown in 7B. Thus, when the drug is injected from the second connector 8 side into the second lumen 117, the drug is all released from the side aperture 125 without escaping from the distal end opening 123. When the guide wire W is pressed against the insertion hole, the valve 127 is elastically deformed by the force from the guide wire W and the guide wire W is allowed to pass through the insertion hole expanded due to the elastic deformation.

The balloon 105 is a bag made of a polyurethane thin film (e.g. having a film thickness of 75 μm in the present embodiment) and has a size large enough to occlude the ascending aorta once inflated. The balloon 105 made of polyurethane has an advantage that when inflated, a desired configuration can be obtained more easily than a balloon made of a rubber material. The balloon 105 has at its both ends, concavities 131 and 132 depressed toward the inside of the balloon 105, and therefore has an apple-like shape as a whole. These concavities 131 and 132 are formed by joining both ends of the balloon 105 to the catheter tube 103 in such a manner that the distance between the two joined parts is shorter than the entire length of the balloon 105.

Figure 8A:
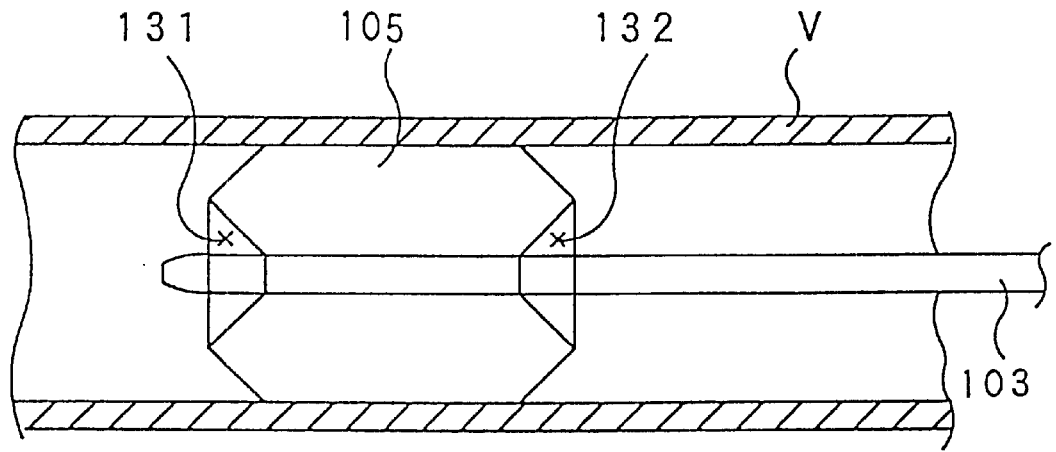
FIGS. 8A through 8C show how concavities provided in the balloon are transformed.
Figure 8B:
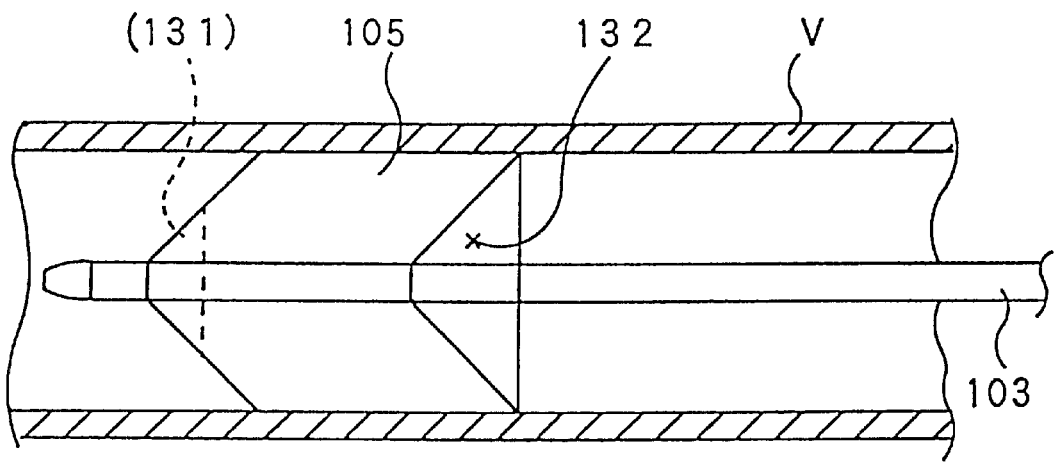
Figure 8C:
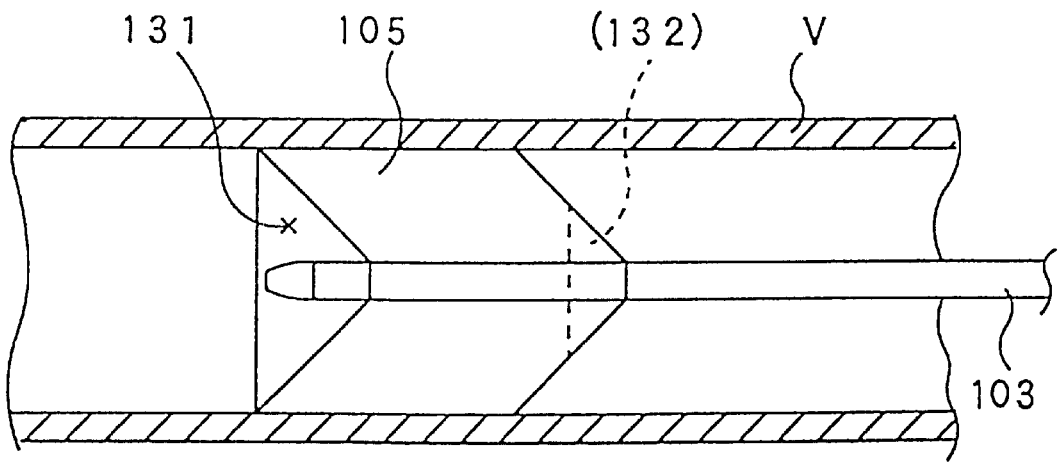

Once the balloon 105 is inflated in the proper indwelling position in the blood vessel V as shown in FIG. 8A and if the catheter tube 103 is displaced for some reason, the concavity 131 becomes convex while the concavity 132 becomes further concave as shown in FIG. 8B. This prevents the balloon 105 from being displaced by following the catheter tube 103. If the catheter tube 103 is displaced in the opposite direction to the above case, the concavity 132 becomes convex while the concavity 131 becomes further concave as shown in FIG. 8C, whereby the balloon catheter 105 is prevented from being displaced by following the catheter tube 103.

The tie cushion 111 is a cylindrical member for preventing the catheter tube 103 from being adversely affected by the force caused when a Nelaton's tube (not shown) is tied and secured to the catheter tube 103 with a thread.

It will now be described how to use the occlusion catheter 101 of the second embodiment.

Firstly, the chest of a patient is incised to expose the ascending aorta and the ascending aorta is perforated to provide a hole in an insertion site thereon. Then, the guide wire W is inserted to secure an insertion route and the hole is expanded with a dilator operated along the guide wire W.

Subsequently, the above occlusion catheter 101 is inserted into the ascending aorta along the guide wire W, and the balloon 105 is placed in the proper indwelling position by locating the balloon 105 using X-ray fluoroscopy. The second lumen 117 in the catheter tube 103 is used as a lumen for guide wire insertion.

Figure 9:
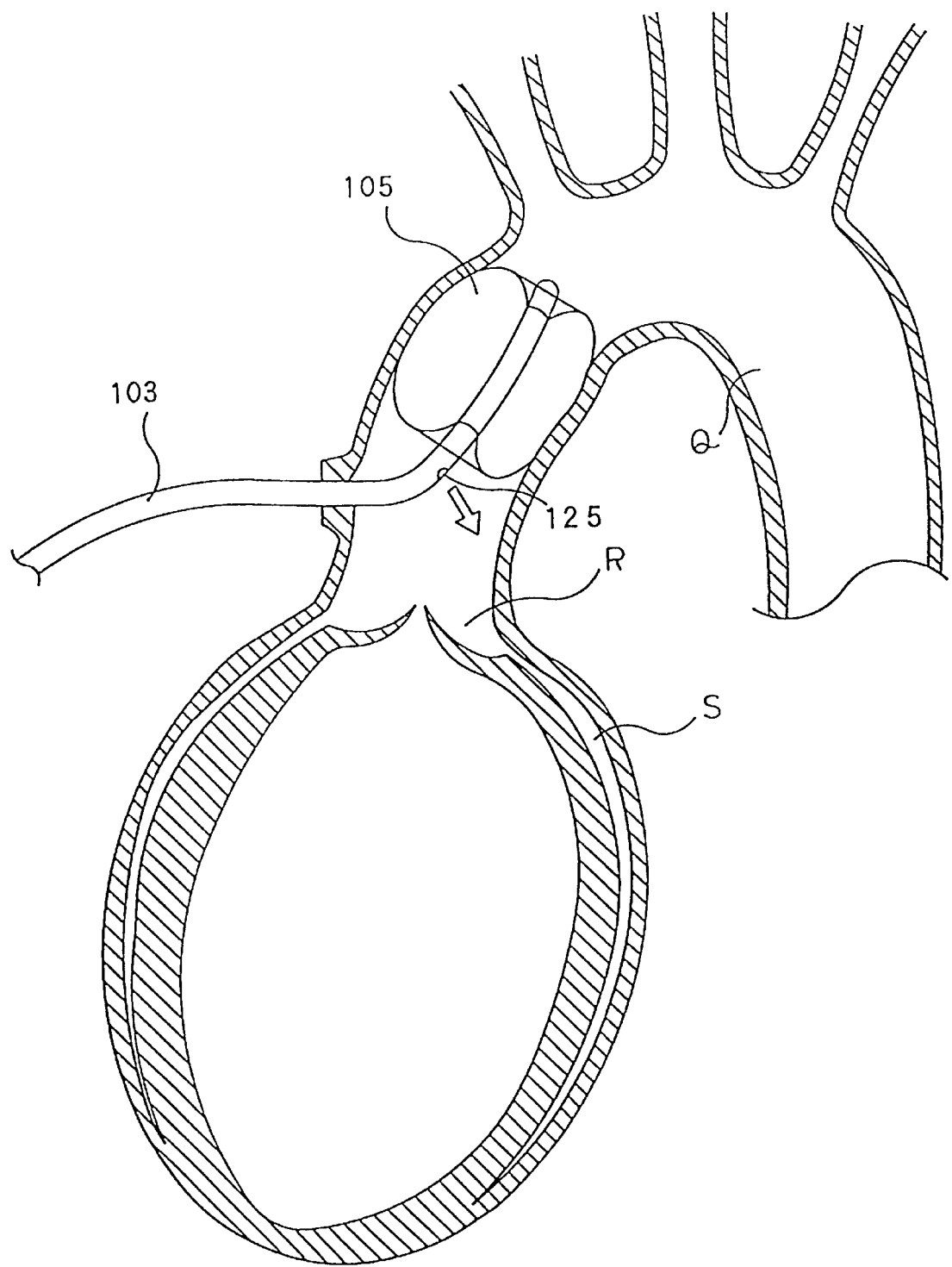
FIG. 9 is a schematic diagram showing the operational state of the occlusion catheter according to the second embodiment.

After the guide wire W is pulled out, the balloon 105 is inflated by supplying an inflation agent through the first lumen 115. As a result, the ascending aorta Q is occluded by the balloon 105, as shown in FIG. 9. The obstruction of the blood flow is to be confirmed by angiography.

When required, a cardiac muscle protective drug is supplied through the second lumen 117 to be released from the side aperture 125 (indicated by the arrow in FIG. 9), with the result that the cardiac muscle protective drug is delivered to the vicinity of the coronary ostium R. While the second lumen 117 is used as a drug delivery lumen in this case, the second lumen 117 is also used for measuring the blood pressure outside the side aperture 125 with a pressure sensor connected to the second connector 8.

As described above, the occlusion catheter 101 with a valve 127 allows the second lumen 117 to be used for three purposes, i.e. for guide wire insertion, drug delivery and blood pressure measurement at the same time. By this, the diameter of the catheter tube 103 can be reduced compared with the catheter tube containing independent lumens corresponding to these purposes, respectively, and therefore the catheter tube 103 can be more flexible. Thus, the displacement of the catheter tube 103 at the proximal end does not directly affect the position of the distal end, and specifically the balloon 105 is not displaced from the proper indwelling position because of a slight displacement of the proximal end of the catheter tube 103.

In the occlusion catheter 101, the displacement of the catheter tube 103 also can be absorbed by deforming the concavities 131 and 132 which are provided for the balloon 105. Therefore, even if the displacement of the catheter tube 103 at the proximal end reaches the distal end, the displacement of the catheter tube 103 at the distal end still does not directly reach the center portion of the balloon 105, which is not displaced from the proper indwelling position because of a slight displacement of the proximal end of the catheter tube 103.

Although the present invention has been described by way of examples, the present invention is not limited to the aforementioned embodiments, and can variously be modified.

For example, although the occlusion catheter 101 is provided with the valve 127 in the catheter tube 103 as well as the concavities 131 and 132 in the balloon 105, the balloon 105 need not be provided with the concavities 131 and 132 if the diameter of the catheter tube 103 is reduced enough, by providing the valve 127 for the catheter tube 103, to achieve the advantage of retaining the balloon 105 in the proper indwelling position.

Oppositely, the catheter tube 103 need not be provided with the valve 127 if the balloon 105 is provided with the concavities 131 and 132 to achieve the same advantage of retaining the balloon 105 in the proper indwelling position. It is also possible to provide a balloon catheter without a lumen for guide wire insertion if not required, wherein the balloon catheter is inserted without using a guide wire and the same advantage of retaining the balloon 105 in the proper indwelling position can be achieved by providing the concavities 131 and 132 in the balloon 105.

Figure 10A:
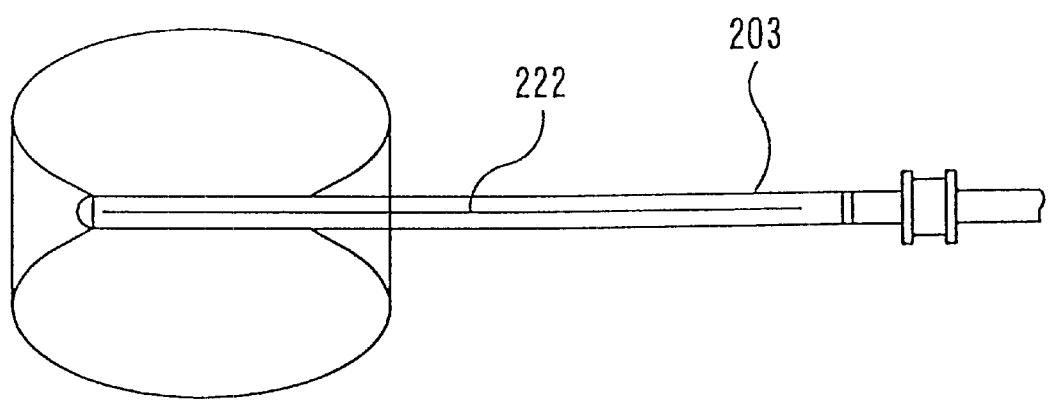
FIG. 10A is a schematic view of an occlusion catheter reinforced with a linear metal wire.
Figure 10B:
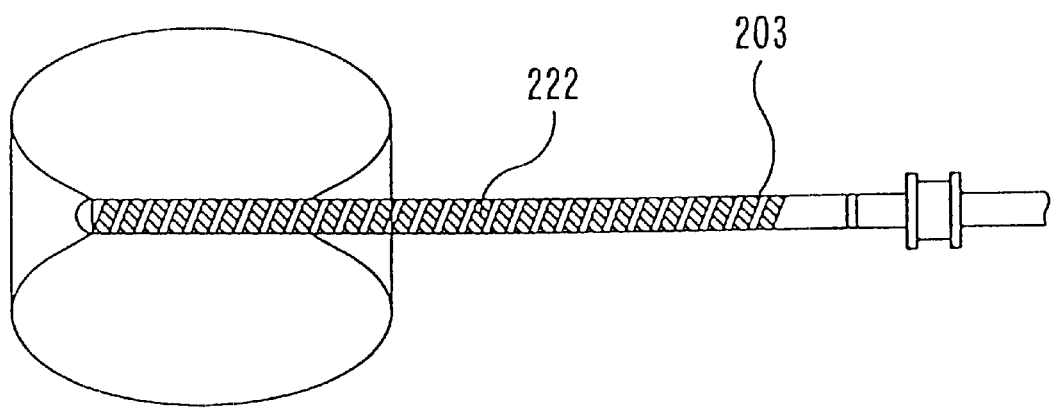
FIG. 10B is a schematic view of an occlusion catheter reinforced with a spiral reinforcing member.

In this case, a catheter tube 203 preferably contains a linear metal wire 222 or a spiral reinforcing member 223 therewithin, as shown in FIG. 10A or FIG. 10B, in order to improve position retainability of the catheter. The material for the metal wire 222 is an elastic material, such as nickel-titanium alloy or stainless steel alloy (e.g. SUS304 according to JIS(Japanese Industrial Standards)), or an inelastic material, such as stainless steel alloy (SUS316 according to JIS) or copper. As the material for the spiral reinforcing member 223, a resin which is harder than the material for the catheter tube 203 may be employed in addition to the above-mentioned materials for the metal wire 222. The metal wire 222 or the spiral reinforcing member 223 has a given length, which preferably ranges from 5 cm to 20 cm, from the distal end of the catheter tube 203.

With the metal wire 222 contained, the catheter tube may have a configuration having the same outer diameter in the portion from the distal end to the midsection (beyond the part to be fixed with the tie cushion toward the proximal end) and having a decreasing outer diameter, i.e. tapered, from the midsection toward the proximal end. This structure can effectively avoid a kink in the catheter which is anticipated being caused due to a sudden change of flexural strength of the catheter on the borderline between the metal wire and a supporting portion for supporting or fastening the wire.

Figure 11A:
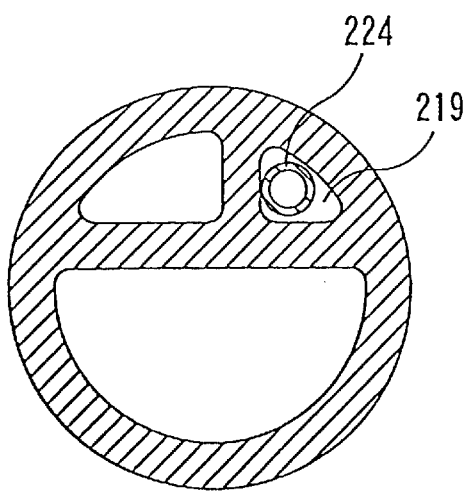
FIGS. 11A through 11D are cross-sectional views showing modified reinforcement members.
Figure 11B:
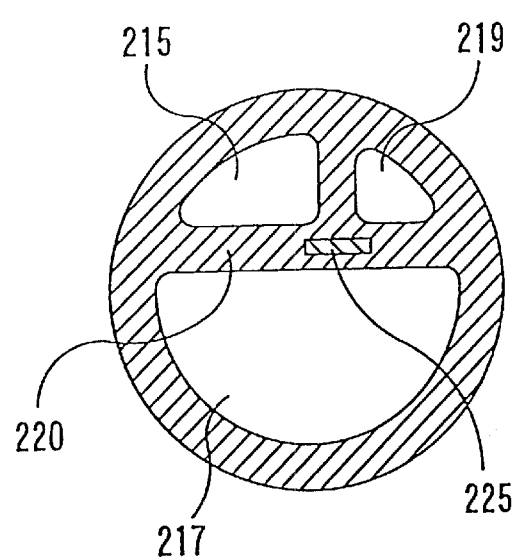
Figure 11C:
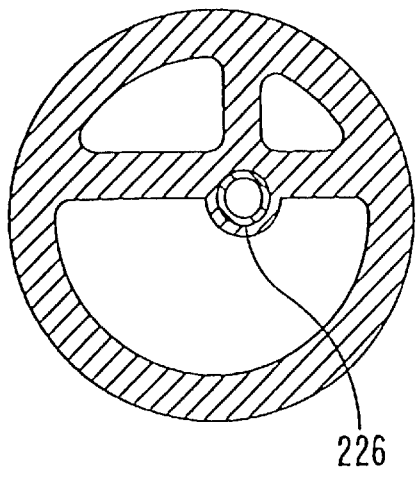
Figure 11D:
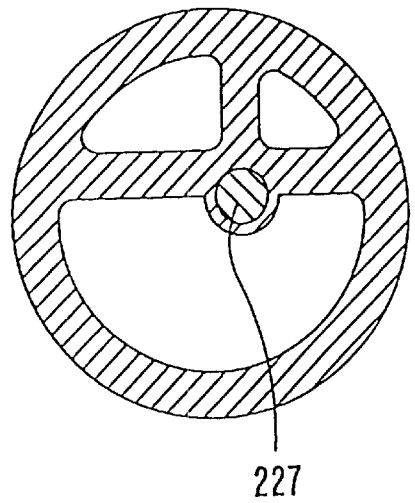

A metal pipe, a flat metal plate or a solid metal cylinder may be employed instead of the linear metal wire 222 or the spiral reinforcing member 223. FIGS. 11A through 11D show these examples. In FIG. 11A, a blood pressure measuring lumen 219 contains a metal pipe 224, which serves to reinforce the front end of the catheter tube and is used for blood pressure measurement with a fluid passing through the pipe. In FIG. 11B, a partition wall 220 separating a first lumen 215 and a third lumen 219 from a second lumen 217 contains a metal plate 225. In FIG. 11C, the partition wall 220 contains a metal pipe 226. In FIG. 11D, the partition wall 220 contains a solid metal cylinder 227.

Although the second lumen 117 in the second embodiment is used for guide wire insertion, drug delivery and blood pressure measurement at the same time by providing the side aperture 125, the second lumen may have a structure without the side aperture 125 if the second lumen 117 is used, for example, for filling a contrast agent therein to obtain images of the catheter tube 103. Even when such a structure is employed, one lumen can be used for both guide wire insertion and contrast agent filling, and therefore the diameter of the catheter tube 103 is reduced to provide an advantage of retaining the balloon 105 in the proper indwelling position.

Although the guide wire W is led out through the side aperture 125 in the second embodiment, the guide wire W may be passed throughout the length of the catheter tube 103. In this case, since it is unnecessary to pass the guide wire W through the side aperture 125, a plurality of openings each opening having a small area may be provided instead of the side aperture 125.

When these plurality of openings are provided in different directions, even if one of the openings is shut by the blood vessel wall, release of the drug is ensured through the rest of the openings. Some of the plurality of openings, of course, may be such that the guide wire W can be inserted thereinto.

Although it has been described that the occlusion catheter 101 is used for obstructing the blood flow in the ascending aorta, the occlusion catheter according to the invention used for obstructing the blood flow in a blood vessel other than the ascending aorta achieves the same advantage that the balloon is retained in the proper indwelling position. Moreover, when the occlusion catheter for ascending aorta according to the present invention is used for widening a narrowed part of a blood vessel, widening effect is further ensured because the balloon can be retained in the proper indwelling position.

Third Embodiment

Figure 12A:
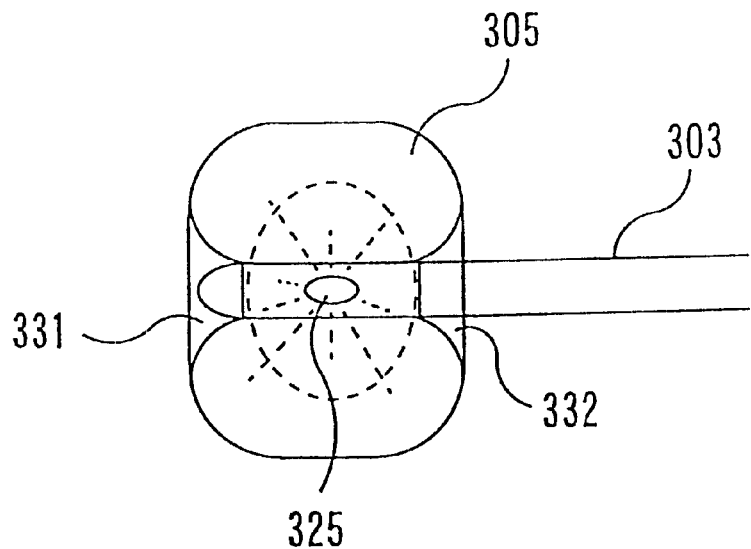
FIG. 12A and FIG. 12B are a front view and a plan view, respectively, in the vicinity of the balloon of an occlusion catheter according to a third embodiment.
Figure 12B:
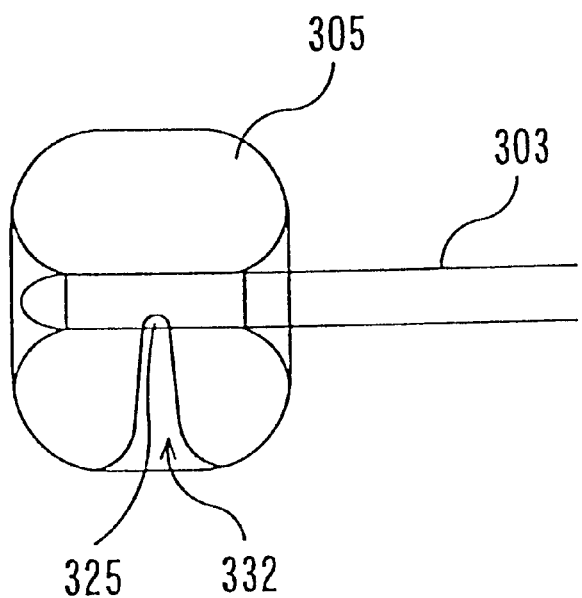

In a third embodiment, a side aperture 325 for releasing the drug therefrom is provided in a catheter tube 303 in the position corresponding to the approximate center of a balloon 305, as shown in FIGS. 12A and 12B. The balloon 305 has concavities 331 and 332 on the outer surface when inflated in the same manner as in the second embodiment, and also has a depression in a part of the center portion of the balloon 305. The balloon 305 is joined to the catheter tube 303 within the depression and the concavities. At the bottom of the depression is provided the side aperture 325 for communicating the second lumen 317 with the outside of the catheter tube 303 (see FIG. 13). Since the other elements are similar to the elements in the first embodiment, particular description is omitted.

Figure 13:
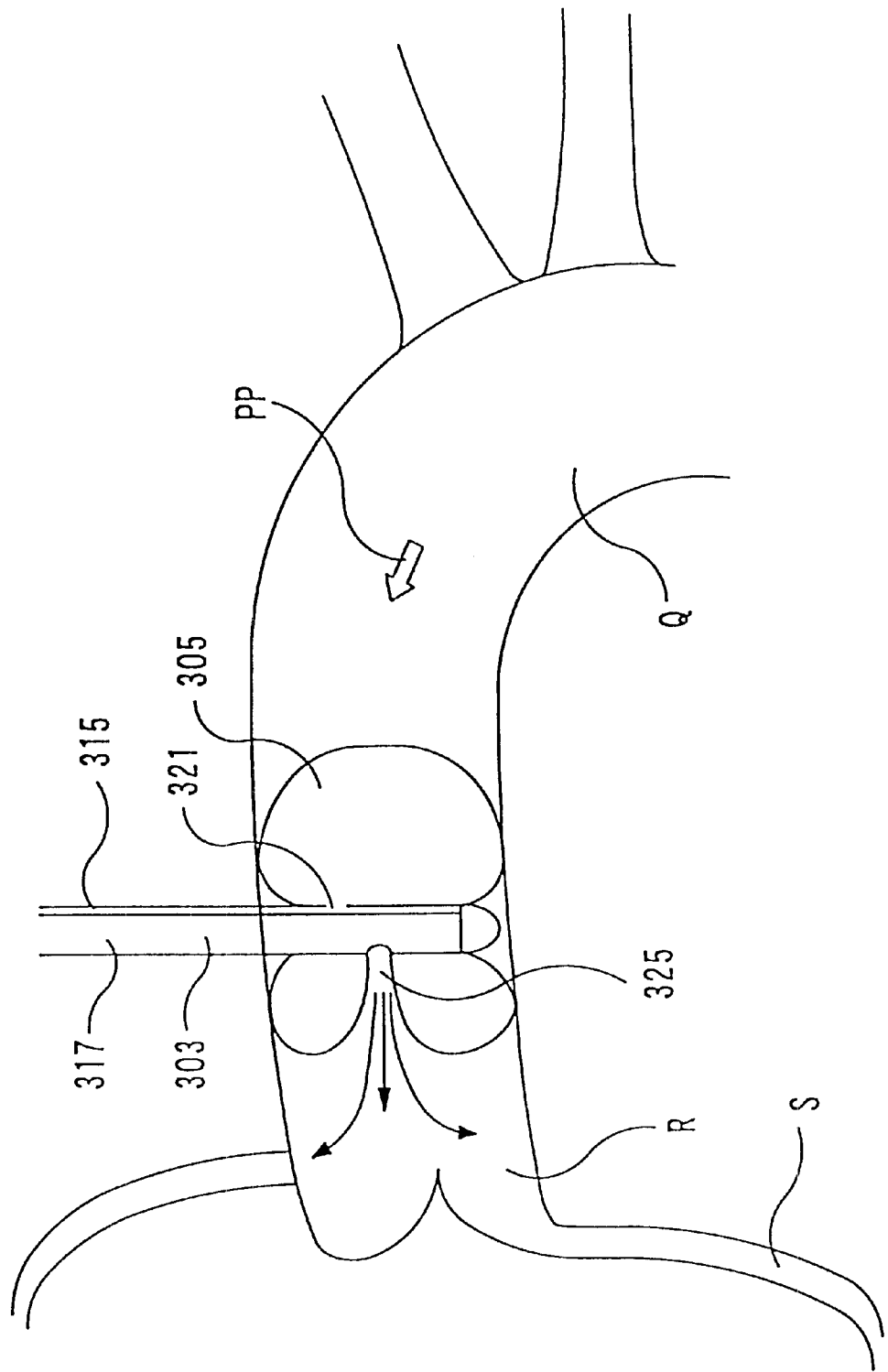
FIG. 13 is a schematic diagram showing the operational state of the occlusion catheter according to the third embodiment.

An occlusion catheter according to the present embodiment, as schematically illustrated in FIG. 13, is inserted into the ascending aorta as in the first and the second embodiments. An inflation agent is injected through an inflation agent supply and drainage aperture 321 to the balloon 305, which is thereby inflated. Once inflated, the balloon 305 is fixed on the blood vessel wall by the pressure from inside the balloon 305. Especially when the catheter tube 303 is inserted approximately perpendicular to the blood vessel, as shown in FIG. 13, improved retainability is achieved since the front and the rear of the catheter tube 303 are symmetrically supported by the balloon.

Thus, even if a pressure PP (indicated by the arrow in FIG. 13) is applied within the artery connected to a pump oxygenator on the opposite side of the heart, the indwelling position of the balloon 305 is not to be changed, that is, improved position retainability is achieved. In such a state, a cardiac muscle protective drug is injected into the vicinity of the coronary ostium R through the side aperture 325. Even if the injection pressure of the cardiac muscle protective drug becomes rather high, the position retainability of the balloon is also secured.

Figure 14A:
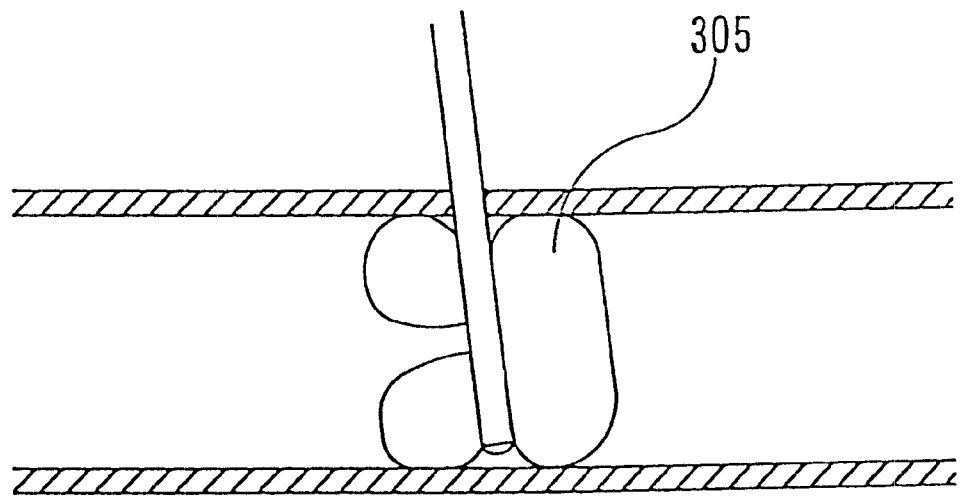
FIG. 14A and FIG. 14B are schematic views illustrating how the balloon according to the third embodiment is retained in an indwelling position.
Figure 14B:
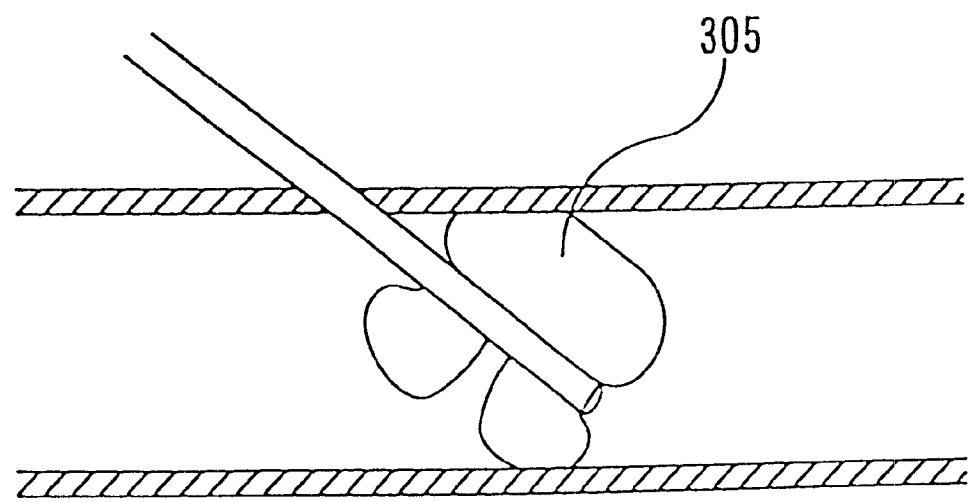

While FIG. 13 shows the state of the occlusion catheter inserted approximately perpendicularly into the ascending aorta, FIGS. 14A and 14B show the state of the occlusion catheter inserted slantingly into the ascending aorta. Even in each of these cases, the total contact area of the balloon 305 with the blood vessel wall does not substantially vary and is large enough to provide a sufficient pressure, so that the position retainability of the balloon is also secured.

Figure 15A:
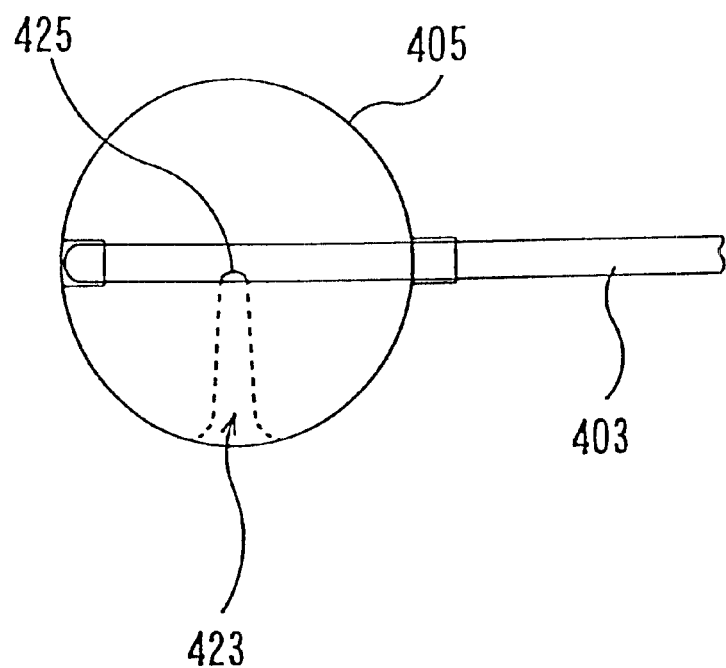
FIG. 15A and FIG. 15B are schematic views showing a modification of the occlusion catheter according to the third embodiment and the balloon used therein.
Figure 15B:
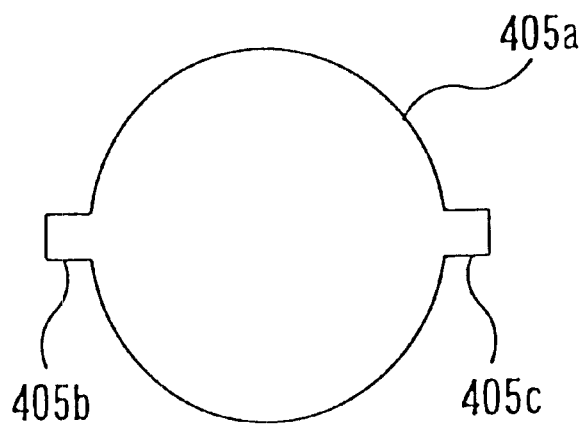

FIG. 15 shows an occlusion catheter with a balloon 405 having a generally spherical configuration except for a depression 433. The balloon 405 shown in FIG. 15A is originally a spherical member 405a shown in FIG. 15B before being fixed to the catheter tube 403. The spherical member 405a has, at its both ends, fixing portions 405b and 405c to be fixed to the catheter tube 403. The fixing portion 405b to be fixed to the front end of the catheter tube 403 is folded back to the inside and joined to the catheter tube 403, while the other fixing portion 405c is joined to the catheter tube 403 as it stands. As shown in FIG. 15A, the cardiac muscle protective drug can be delivered through a side aperture 425 formed in the catheter tube 403. The occlusion catheter shown in FIG. 15A achieves the same position retainability as in FIG. 13.

Although the occlusion catheter according to each of the above-described embodiments is inserted after opening the chest to expose the ascending aorta, such an opening of the chest is not always necessary. For example, it is possible to make a hole in the chest to provide access to the ascending aorta from the outside, and insert the occlusion catheter into the ascending aorta through the hole.

What is claimed is:

1. An occlusion catheter for an ascending aorta comprising:
   a catheter tube having a proximal end and a distal end, and the catheter tube having at least a first lumen and a second lumen separate from the first lumen;
   at least one supply and drainage aperture provided in the catheter tube adjacent the distal end thereof and communicating with the first lumen, a balloon support adjacent the distal end of the catheter tube and communicating with the at least one supply and drainage aperture to facilitate passage of a fluid between the first lumen and the balloon for one of inflating and deflating the balloon as desired a central portion of the balloon being joined to the catheter tube so that the balloon, when inflated, completely obstructs flow of blood through the ascending aorta and forms at least one depression in an outer surface of the balloon where the central portion of the balloon joins to the catheter tube; and
   at least one drug release aperture provided in the catheter tube and communicating with the second lumen, the at least one drug release aperture being located in the catheter tube where the central portion of the balloon join the catheter tube, and the at least one drug release aperture facilitates supply of a drug to the ascending aorta via the second lumen, the at least one drug release aperture and the depression formed in the balloon when the balloon is inflated.

2. The occlusion catheter according to claim 1, wherein the catheter tube is reinforced with a reinforcement member.

3. An occlusion catheter for an ascending aorta comprising:
   a catheter tube having a proximal end and a distal end, and the catheter tube having at least a first lumen and a second lumen;
   at least one supply and drainage aperture provided in the catheter tube adjacent the distal end thereof and communicating with the first lumen, a balloon support adjacent the distal end of the catheter tube and communicating with the at least one supply and drainage aperture to facilitate passage of a fluid between the first lumen and the balloon for one of inflating and deflating the balloon as desired, and the balloon, when inflated, completely obstructing flow of blood through the ascending aorta; and
   a side aperture provided in the catheter tube and communicating with the second lumen, the side aperture being located closer to the proximal end of the catheter tube than the balloon and providing communication with the ascending aorta adjacent the balloon, and the side aperture facilitating supply of a drug to the ascending aorta via the second lumen; and
   a valve provided in the second lumen adjacent the distal end of the catheter tube, the valve being normally closed to prevent passage therethrough, and the valve, when engaged with a guide wire, opening to allow the guide wire to pass therethrough.

4. The occlusion catheter according to claim 3, wherein the valve comprises an elastic body which has a normally closed insertion hole, and the insertion hole opens when the guide wire is inserted through the insertion hole due to elastic deformation of the elastic body.

5. The occlusion catheter according to claim 4, wherein the side aperture allows the guide wire to be inserted therethrough.

6. An occlusion catheter for an ascending aorta comprising:
   a catheter tube having a proximal end and a distal end, and the catheter tube having at least a first lumen and a second lumen separate from the first lumen;
   at least one supply and drainage aperture provided in the catheter tube adjacent the distal end thereof and communicating with the first lumen, a balloon support adjacent the distal end of the catheter tube and communicating with the least one supply and drainage aperture to facilitate passage of a fluid between the first lumen and the balloon for one of inflating and deflating the balloon as desired, and the balloon, when inflated, completely obstructing flow of blood through the ascending aorta; and at least two drug release apertures being provided in the catheter tube and communicating with the second lumen, the at least two drug release apertures being located closer to the proximal end of the catheter tube than the balloon, and the at least two drug release apertures facilitate supply of a drug to the ascending aorta via the second lumen, the at least two drug release apertures extend radially n different directions and the at least two drug release apertures are formed at two different axial locations along the catheter tube.

7. The occlusion catheter according to claim 6, wherein the balloon is manufacture from polyurethane.

8. The occlusion catheter according to claim 6, wherein the catheter tube is reinforced with a reinforcement member.

* * * * *